United States Patent [19]

DiNinno et al.

[11] Patent Number: 4,610,823

[45] Date of Patent: Sep. 9, 1986

[54] PROCESS FOR PREPARING SUBSTITUTED 2-THIOXOPENAMS AND 2-SUBSTITUTED THIOPENEMS

[75] Inventors: Frank P. DiNinno, Old Bridge; William J. Leanza, Berkeley Heights; Ronald W. Ratcliffe, Matawan, all of N.J.

[73] Assignee: Merck & Co., Inc., Rahway, N.J.

[21] Appl. No.: 460,729

[22] Filed: Jan. 25, 1983

[51] Int. Cl.$^4$ ............... C07D 499/04; A61K 31/425
[52] U.S. Cl. ......................... 540/350; 514/195; 540/201; 540/357
[58] Field of Search ............... 260/245.2 R, 265.2 T; 424/270

[56] References Cited

U.S. PATENT DOCUMENTS

| | | | |
|---|---|---|---|
| 4,168,314 | 9/1979 | Christensen | 424/270 |
| 4,215,124 | 7/1980 | Christensen | 424/263 |
| 4,260,618 | 4/1981 | Christensen | 424/263 |
| 4,443,373 | 4/1984 | Girijavallabhan et al. | 260/245.2 R |

FOREIGN PATENT DOCUMENTS

| | | |
|---|---|---|
| 2042514 | 9/1980 | United Kingdom . |
| 2042520A | 9/1980 | United Kingdom . |
| 2074563A | 6/1982 | United Kingdom . |
| 2087880 | 6/1982 | United Kingdom . |

OTHER PUBLICATIONS

J. Chem. Soc. Chem. Commun. No. 13, pp. 713–714 (1982).
Jeffrey & McCombie, J. Org. Chem. 43, 587, 1982.
A. Yoshida, T. Hayoshi, N. Takeda, S. Ohda and E. Olki Chem. Pharm. Bull. 29, 2899 (1981).

*Primary Examiner*—Nicholas S. Rizzo
*Attorney, Agent, or Firm*—Raymond M. Speer; Hesna J. Pfeiffer

[57] ABSTRACT

Disclosed is a synthesis for preparing substituted 2-thioxopenams which are useful in the synthesis of penem antibiotics 7 which may be conducted in an enantiospecific manner; said process proceeds from azetidinone 1 via the azetidinone acetic ester 2, the 4-metallothiozetidinone 3, and the 4-dithiocarbonylazetidinone 4 to the substituted 2-thioxopenam 5:

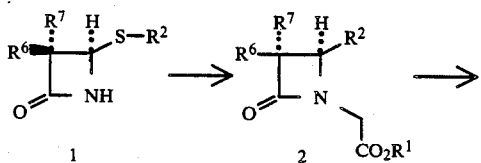

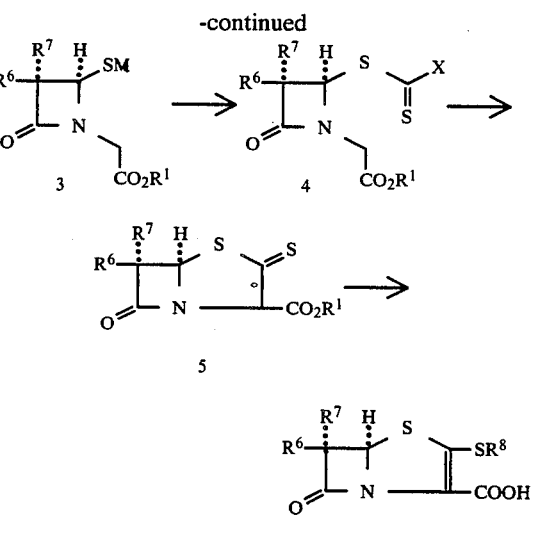

wherein:

$R^6$ and $R^7$ are independently selected from: hydrogen; $R^6NH$— ($R^6$ is acyl or H); substituted and unsubstituted: alkyl, alkenyl, alkynyl, aryl, heterocyclyl, heteroaryl, cycloalkyl, and cycloalkenyl; wherein said substituents are, inter alia: halo (chloro, bromo, fluoro, iodo), hydroxyl, cyano, carboxyl, amino, and the above-recited values for $R^6$ and $R^7$; in functional terms, $R^2$ is a group which potentially forms a stable carbonium ion, for example: trityl (—$C(C_6H_5)_3$), bis(p-methoxyphenyl)methyl,

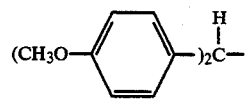

—2,4-dimethoxybenzyl,

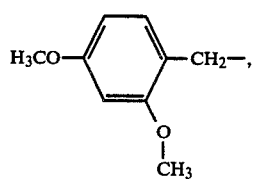

2-(diphenyl)isopropyl,

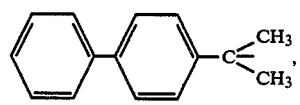

and the like;
M is a thiophilic metal such as silver, thallium, mercury, or the like;

(Abstract continued on next page.)

and $R^1$ is a protecting group such as allyl, p-nitrobenzyl or a biologically removable group (pharmaceutically acceptable ester moiety), for example: pivaloyloxymethyl, pivoloyloxyethyl, ethoxycarbonyloxymethyl, phthalidyl (5-methyl-2-oxo-1,3-dioxolen-4-yl)-; and X is a methyl leaving group such as phenoxy, p-chlorophenoxy, p-nitrophenoxy, phenylthio, alkylthio, alkoxy, chloro, or the like.

$R^8$ is inter alia, substituted and unsubstituted alkyl; the final penem products 7 are known, and their various embodiments are included by this definition.

8 Claims, No Drawings

PROCESS FOR PREPARING SUBSTITUTED 2-THIOXOPENAMS AND 2-SUBSTITUTED THIOPENEMS

BACKGROUND OF THE INVENTION

This invention relates to a process for preparing substituted 2-thioxopenams which are useful in the preparation of known penem antibiotics (7). The process may be conducted enantiospecifically to produce the latter in their correct enantiomeric state necessary for full antibacterial activity.

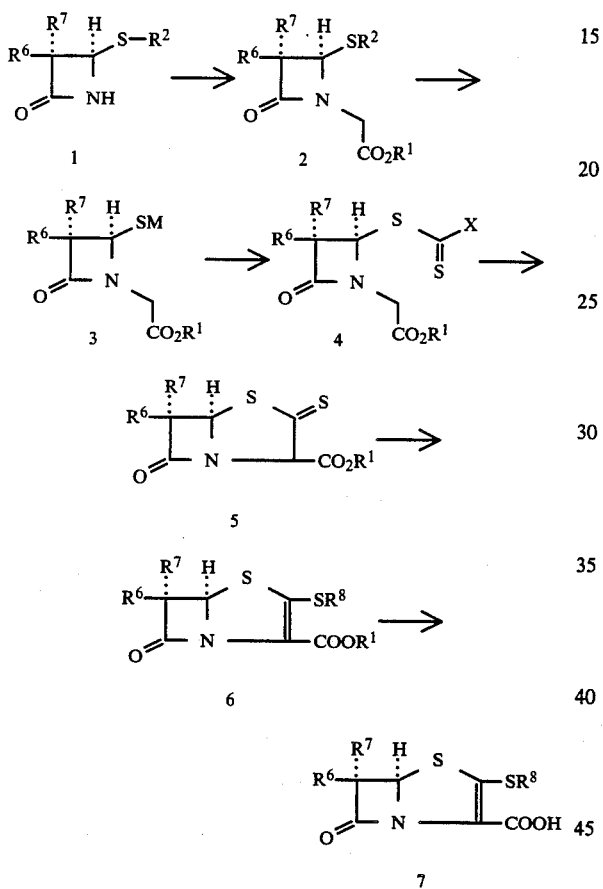

wherein:

$R^6$ and $R^7$ are independently selected from: hydrogen; $R^9NH$—($R^9$ is acyl or H); substituted and unsubstituted: alkyl, alkenyl, alkynyl, having 1-6 carbon atoms; aryl, such as phenyl; heterocyclyl, heteroaryl, having 1-4 heteroatoms selected from O,N,S; cycloalkyl, and cycloalkenyl; wherein said substituent or substituents are selected from: halo (chloro, bromo, fluoro, iodo), hydroxyl, cyano, carboxyl, amino, and the above-recited values for $R^6/R^7$. $R^6$ and $R^7$ are described in detail below; however, it should be noted now that the term "acyl" in the foregoing definition means those acyls known to be effective in the related bicyclic β-lactam antibiotic art, such as the penicillins and cephalosporins. In this regard the definition of acyl recited in U.S. Pat. No. 4,226,866 (issued 10-7-80) is incorporated herein by reference. Also, with respect to $R^6$ and $R^7$, it should be noted that reactive functional groups carried by $R^6/R^7$, such as, amino, hydroxyl, or carboxyl, for example, may be covered by conventional blocking groups, such as p-nitrobenzyloxycarbonyl, 2,2,2-trichloroethoxycarbonyl and triorganosilyl, wherein the organo moiety is selected from alkyl having 1-6 carbon atoms, phenyl, and phenylalkyl.

$R^2$, in functional terms, is a group which potentially forms a stable carbonium ion, for example: trityl; $(-C(C_6H_5)_3)$;

bis(methoxyphenyl)methyl,

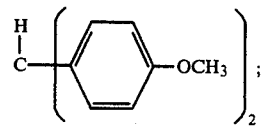

2-(diphenyl)isopropyl,

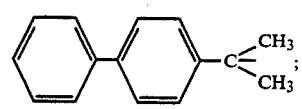

2,4-dimethoxybenzyl,

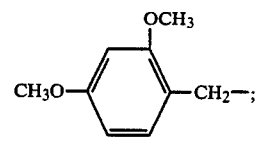

and the like.

M is a thiophilic metal such as silver, thallium, mercury, or the like.

$R^1$ is a removable protecting group such as allyl, p-nitrobenzyl, or a biologically removable group, for example: pivaloyloxymethyl, pivoloyloxyethyl, ethoxycarbonyloxymethyl, phthalidyl, or the like; in short, $R^1$ is selected from any of the conventionally employed protecting groups, or pharmaceutically acceptable ester moieties known in the classical (penicillins, and cephalosporins) and nonclassical (e.g., carbapenems, and penems) β-lactam antibiotic art (see for example, U.S. Pat. No. 4,226,866, which is incorporated herein by reference to the extent that it discloses such ester moieties).

X is a leaving group such as substituted or unsubstituted: phenoxy, alkoxy, phenylthio, or alkylthio having 2 to 7 carbon atoms; halo (chloro or bromo), and the like, wherein, for example, such substituents are: chloro, nitro, methyl, and the like.

$R^8$, representatively defined below, is, inter alia, substituted and unsubstituted: alkyl, aryl, heteroaryl, heterocyclyl, and the like; wherein the substituent or substituents are selected from: amino, cyano, amidino, carbamoyl, hydroxyl, acyl, acyloxy, carboxy, and the like.

The ultimate penem antibiotics 7, including the foregoing definitions for $R^1$, $R^6$, $R^7$ and $R^8$, are representatively disclosed in the following publications and pending U.S. Patent applications, all of which are incorporated herein by reference for the purpose of defining 7 and its utility as an antibiotic: U.S. Pat. No. 4,260,618 (4/7/81); U.S. Pat. No. 4,215,124 (7/29/80); U.K. Patent Application G.B. No. 2013674A (8/15/79); U.K.

Patent Application G.B. No. 2042520A (9/24/80); and U.S. patent application Ser. Nos. 353,451, filed Mar. 1, 1982; 353,450, filed Mar. 1, 1982; 353,454, filed Mar. 1, 1982; 353,453, filed Mar. 1, 1982; and 373,008, filed Apr. 29, 1982.

The conversion process of appropriately substituted 2-thioxopenams 5 to the corresponding antibiotic 2-$SR^8$-pen-2-em-3-carboxylic acids 6 is known; as is the final deblocking step 6 to 7:

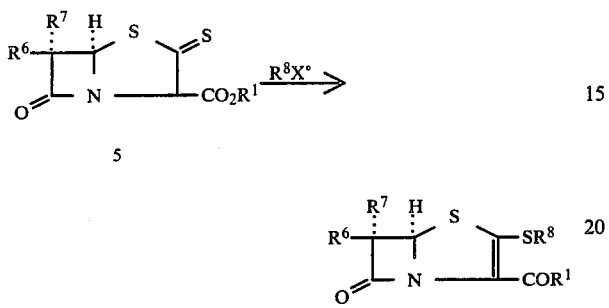

wherein $R^8X^\circ$ is an alkylating agent; $X^\circ$ is bromo or iodo, for example; and $R^8$ is as defined above, for example, cyanomethyl, cyanoethyl, or the like. $R^8$ is additionally defined below. With respect to the formation of 5 and its conversion to 6, see U.K. Patent Application GB No. B 2074563A; or J. Chem. Soc. Chem. Cummun. No. 13, pp 713–714 (1982), which are fully incorporated herein by reference.

In the previous process referred to above (wherein $R^6$ is hydrogen and $R^7$ is protected hydroxyethyl) the thioxopenams are prepared by a distinctly different process where the $C_5$–$C_6$ positions have the cis configuration. This is a result of two factors. First, the 3-substituted-4-alkylthioazetidinone intermediates are obtained with the $C_3$–$C_4$ trans configuration and, second, the ring closure step involves displacement at the $C_4$ carbon atom causing an inversion at this position. Thus the known alkylation of the cis-thioxopenams produces the undescribed and antibacterially inferior 5,6-cis-2-alkylthiopenems which are converted to a mixture containing the 5,6-trans-penems by a thermal equilibration. The present invention maintains the stereochemical integrity of the substituent on the intermediate azetidinone throughout the conversion to thioxopenams and alkylthiopenems. Thus it provides the preferred 5R,6S-6(1-R-hydroxyethyl)penems from the azetidinone nucleus derived from 6-aminopenicillanic acid.

DETAILED DESCRIPTION OF THE INVENTION

The following diagram conveniently summarizes the process of the present invention:

DIAGRAM I

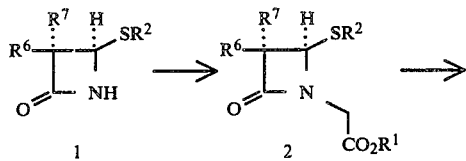

-continued
DIAGRAM I

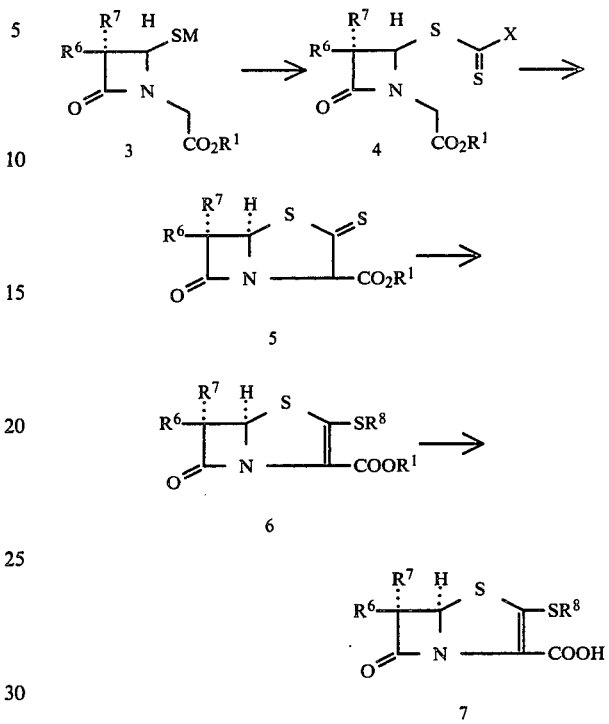

In words relative to the above diagram, the azetidinone starting material 1 is known, or can readily be prepared by known methods. Representative, and representatively preferred values for $R^6$ and $R^7$ are given below. $R^2$ in starting material 1 must be a group which allows the formation of a carbonium ion. Preferred values for $R^2$ include, trityl, bis(p-methoxyphenyl)-methyl, 2,4-dimethoxybenzyl, and the like. The most preferred value for $R^2$ is trityl. As defined above, the most preferred values for $R^1$ include allyl, p-nitrobenzyl, and the like. The conversion 1 to 2 is accomplished by treating 1 in a solvent such as benzene, toluene, xylene, DMF, or the like, in the presence of powdered fused potassium hydroxide, sodium hydride, potassium t-butoxide, Triton B or the like, and 18-crown-6 or a tetraalkylammonium salt, or the like with a bromoacetic ester such as allylbromoacetate, p-nitrobenzylbromo acetate, or the like, for from 0.5 to 4 hours at a temperature of from 0° to 80° C.

The conversion 2 to 3 is accomplished by treating 2 in a solvent such as methanol, ethanol, butanol, or solvent mixtures such as methanolmethylene chloride, or the like, in the presence of pyridine, picoline, lutidine, 4-dimethylaminopyridone, or the like, with a thiophilic metal salt reagent such as silver, mercury, thallium, nitrate, triflate, acetate, or the like, for from 0.1 to 3 hours at a temperature of from 0° to 60° C. The most preferred thiophilic metal is silver, and the most preferred silver reagent is silver nitrate.

The conversion 3 to 4 is accomplished by treating 3 in a solvent such as methylene chloride, benzene, tetrahydrofuran, or the like, with a halothiocarbonate ester of the formula:

wherein: X'=chloro, bromo, and X is an aryloxy, arylthio, alkylthio, alkoxy or halo group, for example, in the presence of pyridine, picoline, lutidine, 4-dimethylaminopyridine, or the like, at a temperature of 0° to 30° C. for from 0.5 to 2 hours. [In the foregoing, alkyl is 1-6 carbon atoms; and aryl is phenyl.]

In general, the cyclization 4 to 5 is accomplished in the presence of base. For example, cyclization 4 to 5 may be accomplished by treating 4 in a solvent such as tetrahydrofuran, toluene, ether, dioxane, or the like, or mixtures thereof in the presence of lithium hexamethyldisilazide, lithium 2,2,6,6-tetramethyl piperidide, lithium triethyl methoxide, sodium hydride, potassium t-butoxide, or the like, in the presence of hexamethylphosphoramide, 1,3-dimethyl-2-imidazolidinone (DMF) or the like, at a temperature of from −78° to 23° C. for from 0.1 to 8 hours. Alternatively, the conversion of 4 to 5 is accomplished by treating 4 in a solvent such as, methylene chloride, chloroform, tetrahydrofuran, benzene, or the like, in the presence of 1,8-diazabicyclo[5.40] undec-7-ene, diisopropylethylamine, 1,5-diazabicyclo[4.3.0]non-5-ene; 1,8-bis(dimethylamino)-naphthalene, or the like, at a temperature of from 20° to 80° C. for from 1 to 18 hours.

The conversion 5 to 6 is accomplished by treating the 2-thioxopenam in a solvent such as methylenechloride, dimethoxyethane, dimethylformamide, or the like, at a temperature of from −25° to 100° C. with an alkylating agent $R^8X°$; wherein $R^8$ is alkyl, alkenyl, aralkyl, heteroaralkyl, alkynyl, or heterocyclyl; and X° is a leaving group such as halo, arylsulfonate, trifluoromethyl sulfonate, or the like, or with an alkanol, diethylazodicarboxylate, and triphenyl phosphene, and the like.

The final deblocking step 6 to 7 is accomplished by conventional procedures such as hydolysis or hydrogenation. Typically 6 when $R^1$ is p-nitrobenzyl in a solvent such as dioxane-water-ethanol, tetrahydrofuran-aqueous dipotassium hydrogen phosphate-isopropanol, or the like, is treated under a hydrogen pressure of from 1 to 4 atmosphere in the presence of a hydrogenation catalyst such as palladium on charcoal, palladium hydroxide, or the like at a temperature of from 0° to 50° C. for from 0.5 to 4 hours to provide 7.

When $R^1$ is allyl, the ester is removed by the method of Jeffrey and McCombie, J. Org. Chem. 43, 587 (1982). Typically the penem allyl ester is stirred in a solvent such as methylene chloride, ethylacetate or tetrahydrofuran with potassium or sodium 2-ethylhexanoate and a catalytic amount of tetrabistriphenylphosphine palladium (O) at ambient temperature for from 15 minutes to 1 hour. The potassium salt of the penem usually precipitates from solution or may be precipitated by the addition of Et$_2$O and is recovered by filtration. When $R^7$ is a protected hydroxyalkyl group the hydroxy protecting group may be removed prior to or simultaneously with the removal of the ester blocking group. Typically when the protecting group is tert-butyldimethylsilyl it is removed prior to deesterification by treatment with 3 eq. of tetrabutylammonium fluoride buffered with 10 eq. of glacial acetic acid in tetrahydrofuran solution at 23° for 24-72 hours. When the hydroxy protecting group is p-nitrobenzyloxycarbonyl and the ester group is p-nitrobenzyl they are removed simultaneously by hydrogenation (above).

PREPARATION OF STARTING MATERIAL

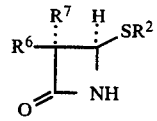

Starting materials 1 are known, or are prepared according to known methods. The most preferred situation finds $R^6$=H and $R^7$ as defined above, such as, alkyl having 1-6 carbon atoms and hydroxyl-substituted alkyl, for example, CH$_3$CH(OH); wherein the hydroxyl function is typically protected by a triorganosilyl group, such as, t-butyldimethylsilyl (TBDMS), or the like. The racemic tritylthioazetidinone 1 may be prepared according to U.K. Pat. No. 2,042,514 (1980), which is incorporated herein by reference; the preferred chiral azetidinone 1 ($R^6$=H, $R^7$=protected hydroxyethyl) can be prepared from 6-APA by the method of A. Yoshida, T. Hayoshi, N. Takeda, S. Ohda and E. Olki Chem. Pharm. Bull. 29, 2899 (1981), citing the procedure of F. Di Ninno, U.S. Pat. No. 4,168,314 (1979) and J. Org. Chem. 42, 2960 (1977) who used a p-nitrobenzyl (PNB) blocking group on the OH instead of TBDMS. These publications are all incorporated herein by reference. Other, representative values of $R^6$ and $R^7$ are listed below.

DEFINITION OF $R^6$ and $R^7$

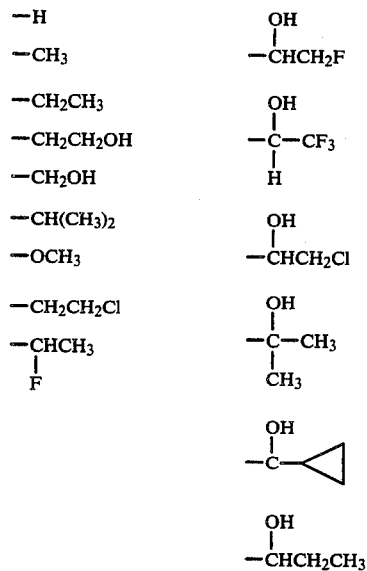

DEFINITION OF $R^8$

Representative values for $R^8$ include:
CH$_3$, —CH$_2$CH$_3$, —CH$_2$CONH$_2$, CH$_2$CN, CH$_2$CH$_2$OH, CH$_2$CH$_2$CN, CH(Me)CH$_2$CONH$_2$, CH(Me)CH$_2$CN, CH$_2$(CH$_3$)CHCN,

CH$_2$COCH$_3$,

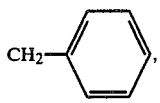

$CH_2CO_2R$, where R=Me, Et, allyl or pharmaceutically acceptable ester.

The most preferred 2-thioxopenams bear at ring position number 6 the 1-hydroxyethyl substituent. The most preferred configuration of these thioxopenams is 8R, 6S, 5R.

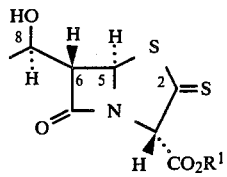

With regard to the preparation of the preferred 2-thioxopenams of the present invention, the following diagram specifically recites their synthesis.

R=t-butyldimethylsilyl
φ=phenyl
$R^1$=$CH_2CH$=$CH_2$ or p-nitrobenzyl (PNB)

Step I

In the preferred process (3R,4R)-4-acetoxy-3-[(R)-1-(tert-butyldimethylsilyloxy)ethyl]-2-azetidinone (1) is stirred with sodium triphenylmethylmercaptide in DMF solvent at 0° C. for 45 minutes to produce after workup and isolation (3S,4R)-4-triphenylmethylthio-3-[(R)-1-(tert-butyldimethylsilyloxy)ethyl]-2-azetidinone (2). Alternatively intermediate (2) can be produced by exposure of 1 to tritylmercaptan in methanolic soidum methoxide.

Step II

The tritylthioazetidinone 2 is treated with 1.5 equivalents of allyl bromoacetate and powdered potassium hydroxide in benzene solvent at ambient temperature in the presence of dicyclohexyl-18-crown-6 for 4 hours. The resulting (3S,4R)-1-(allyloxycarbonyl)methyl-3-[(R)-1-(tert-butyldimethylsiloxy)-ethyl]-4-triphenylmethylthio-2-acetidinone (3) is isolated by conventional

DIAGRAM II

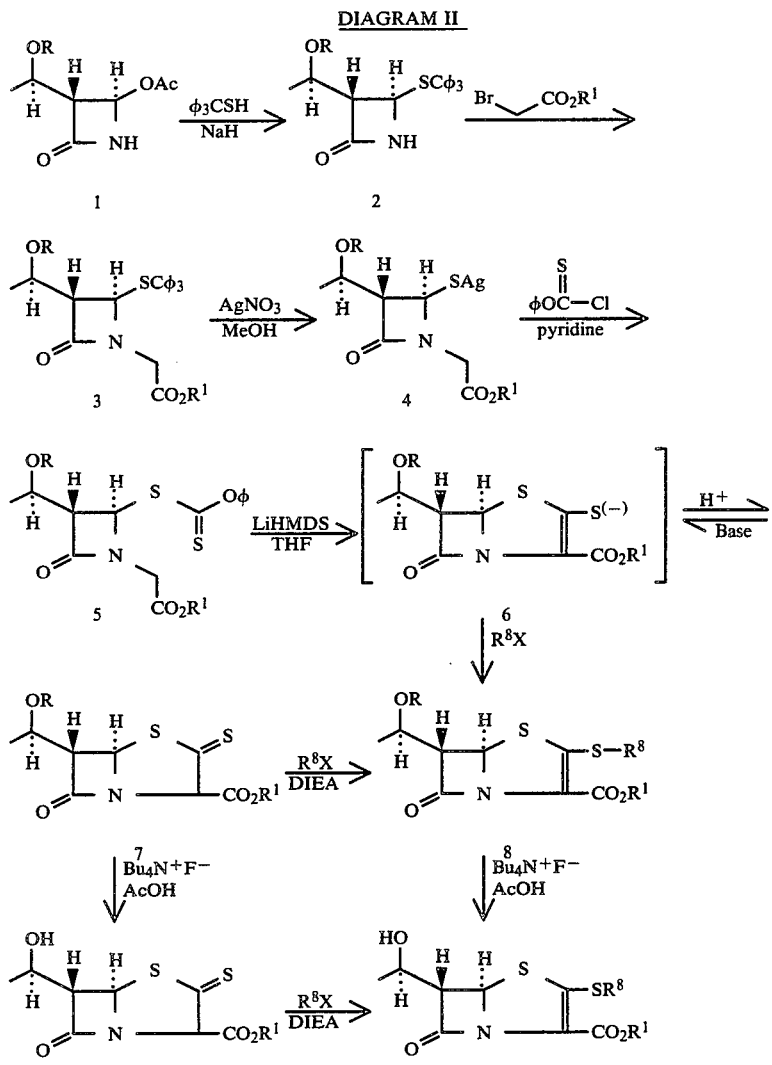

means. Alternatively p-nitro-benzylbromoacetate may be substituted for allylbromoacetate.

Step III

The azetidinone 3 is treated with a methanolic solution of silver nitrate in the presence of pyridine in methanol solvent at 0° C. for 0.5 hours. After removal of the water-soluble salts the crude mixture containing the silver thiolate 4 is preferably carried into the next step but may be purified by conventional techniques, such as preparative thin layer chromatography. The solvent methanol employed herein serves a dual purpose in that it reacts with the incipient trityl carbonium ion to form trityl methyl ether, which need not be separated from the silver thiolate, as it is inert to the reagents used in Step IV and may be conveniently separated later. The process of forming silver thiolates from 4-tritylthioazetidinone and their acylation has been described in the U.K. Pat. No. 2,042,520A, which is incorporated above. This invention adopts that process to specifically form a 4-dithiocarbonate ester of an azetidinon-1-yl acetic ester giving the critical intermediate 4 for the hitherto unknown cyclization reaction in Step V.

Step IV

The crude silver thiolate obtained from Step III is thioacylated with phenoxythiocarbonyl chloride in methylene chloride solvent in the presence of pyridine at 0° C. for 20 minutes. The chlorothiocarbonate ester employed herein is not critical, however, the leaving group X should not be so reactive that is undergoes elimination under the conditions of the thioacylation reaction, leading to side reactions; nor so wealkyl reactive that it is displaced with difficulty during Step V. Phenoxy acid substituted phenoxy are preferred for group X, although alkoxy, alkylthio and arylthio may be used. From 0.1 to 1.0 equivalents of pyridine or a similar organic base is used to catalyze the reaction. In the preferred case it is not necessary to purify the resulting phenoxythiocarbonyl derivative 5 for use in the next step, particularly if purified silver thiolate is used in the reaction.

Step V

Purified (3S,4R)-1-(allyloxycarbonyl)methyl-3-[(R)-1-(tert-butyldimethylsilyloxy)ethyl]-4-phenoxy(thiocarbonyl)thio-2-azetidinone (5) is treated with 2.75 equivalents of the preferred base lithium hexamethyldisilazide at −78° C. in anhydrous tetrahydrofuran containing some 1,3-dimethyl-2-imidazolidinone (DMI), which appears to make the reaction proceed more uniformly, under an atmosphere of nitrogen. After 5–15 minutes, the mixture is neutralized with dilute hydrochloric acid, although other organic acids such as acetic, trifluoroacetic, and p-toluenesulfonic acids, as well as aqueous buffers, may be used, and worked up to give the desired 2-thioxopenams 7. Since the initial product of the reaction is the thiolate anion 6, it may be treated in situ if desired with the alkylating agent to directly give penem derivatives. Alternatively, a strong organic base such as diazabicycloundecene (DBU) will give slow cyclization of 5 to 7 at room temperature.

Although in the preferred process the hydroxy group is protected by a t-butyldimethylsilyl group, the presence of this group is not necessary during all of the steps in the reaction sequence. It may be conveniently removed from the thioxo penam (7) either before or after alkylation or it may be removed earlier in the sequence (e.g., from 3) and be replaced with a more readily hydrolyzable group such as trimethylsilyl just before the cyclization to (6).

EXAMPLE 1

Allyl-trans-2-(3-(1-t-butyldimethylsilyloxyethyl)-4-silverthio-2-azetidinon-1-yl)acetate

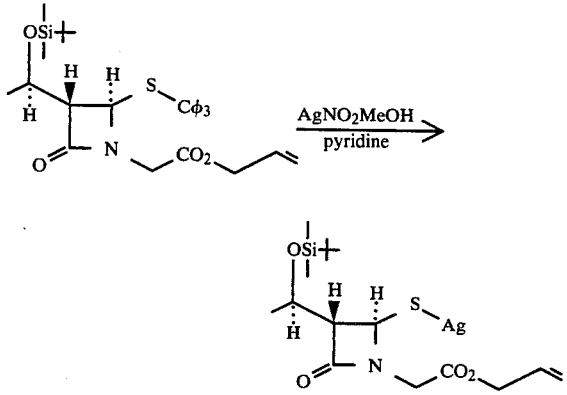

To a solution of allyl trans-2-(3(1-t-butyldimethylsilyloxyethyl)-4-triphenylmethylthio-2-azetidinon-1-yl)acetate (126 mg, 0.223 mmol) in 1 ml of methanol at 0° was added pyridine (27 μl) followed by a solution of silver nitrate in methanol (2.32 ml of 0.12M solution). After stirring for 30 minutes, the methanol was rapidly evaporated under vacuum and the residue was taken up in 7 ml of methylene cloride. The solution was washed three times with 8 ml portions of water, dried over anhydrous magnesium sulfate and evaporated. The residue was chromatographed on a thin layer silica gel plate eluted with toluene-ethyl acetate (7:3). The band between 4.5 and 11 cm was extracted with methanol to afford the desired product. Yield 76 mg, (73%) of a white solid. NMR δ (200 MHz, CDCl₃), 3.10 (dd, J=4.2 and 1.8, H3), 5.21 (d, J=1.8, H4).

EXAMPLE 2

Allyl-trans-2-(3-(1-t butyldimethylsilyloxyethyl)-4-phenoxythiocarbonylthio-2-azetidinon-1-yl)acetate

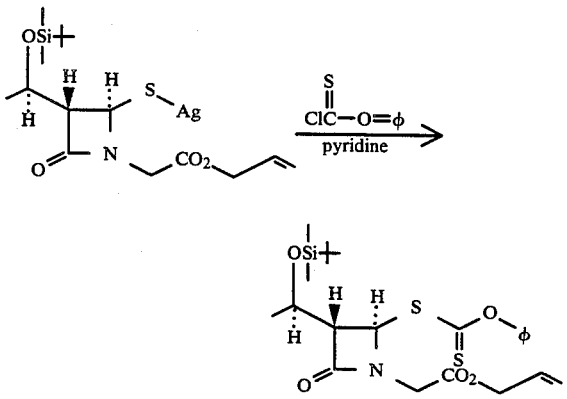

To a cooled (0°) solution of allyl trans 2-(3-(1-t butyl-dimethylsilyloxyethyl)-4-silverthio-2-azetidinon-1-yl)acetate (104 mg, 0.223 mmol) in 4 ml of methylene chloride was added phenoxythiocarbonyl chloride (30

μl, 0.223 mmol) followed by pyridine (18 μl). After 20 minutes the solution was evaporated to dryness under reduced pressure. The residue was taken up in methylene chloride and the precipitated silver chloride was removed by filtration. The filtrate was concentrated and chromatographed on a silica gel plate developed with 9:1 toluene-ethyl acetate. The band at 5.5-8.5 cm was isolated with ethyl acetate. Yield 69 mg, (62%) of product as an oil. NMR δ (200 MHz, CDCl₃), 3.34 (dd, J=6 and 2.5, H3), 5.88 (d and m, J=2.5, H4 and vinylic methylene).

EXAMPLE 3

Allyl-trans-6-(1-t-butyldimethylsilyloxyethyl)-2-thioxopenam-3-carboxylate

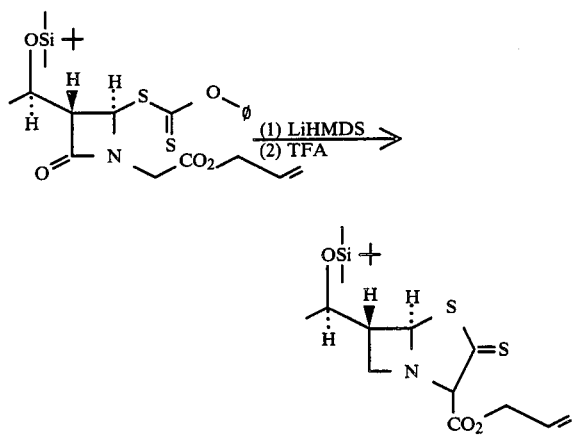

A solution of butyllithium (217 μl of 2.3M solution in hexane) was added to a solution of hexanethyldisilizane (106 μl) in tetrahydrofuran (0.68 ml) at room temperature. After 30 minutes, the solution was cooled to −78° and added to a cooled (−78° ) solution of allyl trans 2-[3-(1-t-butyldimethylsilyloxyethyl)-4-phenoxythiocarbonylthio-2-azetidinon-1-yl)acetate (100 mg, 0.17 mmol) in 1 ml tetrahydrofuran. The solution was stirred for 20 minutes then neutralized with trifluoroacetic acid (15 μl). The solution was diluted with methylene chloride (8 ml) and washed successively with 0.1M, pH 7 phosphate buffer (6 ml) and water (2×6 ml), then dried (MgSO₄) and evoporated. The product was purified by thin layer chromatography eluted with methylene chloride-toluene (6:1). Yield 68 mg, (84%). NMR δ (200 MHz, CDCl₃), 3.65 (d, J=1.5, H6), 5.35 (s, H3 and m, vinylic methylene), 5.9 (s, H5 and m, vinylic methine).

EXAMPLE 4

Ally-trans-(6-(1-t-butyldimethylsilyloxyethyl)-2-methylthiopenem-3-carboxylate

Procedure A

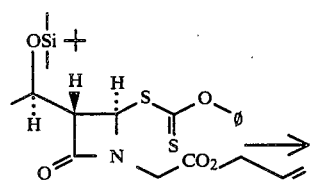

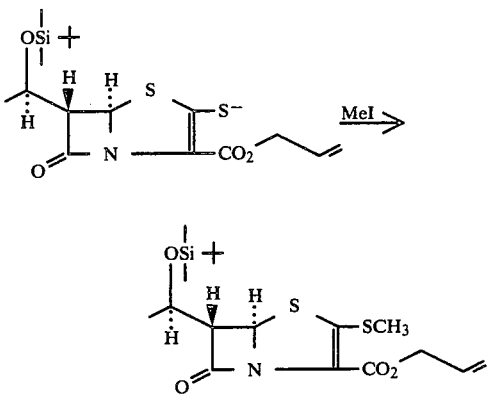

To a solution of penem thiolate prepared as in Example 3 from allyl trans 2-[3(1-t-butyldimethylsilyloxyethyl)-4-phenoxythio-carbonylthio-2-azetidinon-1-yl)acetate (18.1 mg, 0.036 mmol) and lithium hexamethyl disilazide (420 μl of 0.175M solution), methyl iodide (20 μl) was added and the solution is allowed to come to room temperature. The reaction mixture was diluted with methylene chloride, washed with water, dried over magnesium sulfate and evaporated. The residue was purified by thin layer chromatography developed with 9:1 toluene-ethyl acetate giving 8.8 mg (58%) of the desired methylthiopenem, U/V λmax. 337 mμ (ε6150), 256 mμ (ε5480). NMR δ (200 MHz,CDCl₃), 2.53 (s, SCH₃), 3.66 (dd, J=5.2 and 1.5, H6), 5.65 (d, J=1.5, H5).

Procedure B

A solution of allyl trans 2-[3(1-t-butyldimethylsilyloxyethyl)-4-phenoxythiocarbonyl]thio-2-azetidinon-1-yl)acetate (12.2 mg, 0.025 mmol) and 1,8-diazabibyclo[5.4.0]undec-7-ene (7.4 μl) in 0.4 ml of THF was stirred at 23° for 8 hours. To the resulting solution of thioxopenam was added methyliodide (20 μl) and the solution was stirred for one hour. The solution was worked up as in procedure A to give 4.8 mg of the above described methylthiopenem.

EXAMPLE 5

P-nitrobenzyl-trans-2-[3-(1-t-butyldimethylsilyloxyethyl)-4-triphenylmethylthio-2-azetidinon-1-yl)acetate

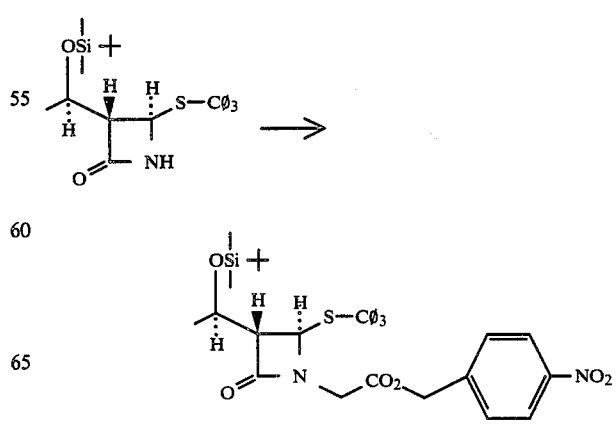

Powdered, fused potassium hydroxide (125 mg, 2.25 mmol) and 18-crown-6 (20 mg) were added to a solution of 3-(1-t-butyldimethylsilyloxyethyl)-4-triphenylmethylthio-2-azetidinone (775 mg, 1.5 mmol) in 7 ml of benzene. The mixture was stirred at room temperature while a solution of P-nitrobenzyl bromoacetate (620 mg, 2.25 mmol) in benzene (7 ml) was added dropwise during one hour. After an additional hour of stirring, 0.5M, pH 7 phosphate buffer (20 ml) was added and the benzene layer was separated, dried (MgSO4) and evaporated. The residual oil was chromatographed on silica gel (2×25 cm column) eluted with methylene chloride. There was first obtained a fraction containing starting azetidinone (230 mg) followed by the desired product (710 mg, 68% yield). NMR δ (200 MHz, CDCl3), 3.42 (t, J=2.3, H3), 4.56 (d, J=2.3, H4).

EXAMPLE 6

P-nitrobenzyl-trans-2-[3-(1-t-butyldimethylsilyloxyethyl)-4-silverthio-2-azetidinon-1-yl)acetate

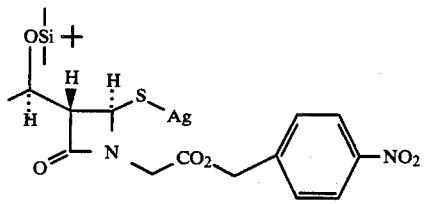

To a cooled (0°) solution of P-nitrobenzyl trans 2-[3-1-t-butyldimethylsilyloxyethyl)-4-triphenylmethylthio-2-azetidinon-1-yl)acetate (55 mg, 0.079 mmol) in 1 ml of methanol was added pyridine (10 μl) and 0.12M silver nitrate in methanol (0.82 ml). A precipitate immediately formed. The mixture was stirred at 0° for 30 minutes then the precipitate was recovered by filtration, washed with methanol and dried under nitrogen giving a white powder (44 mg). This was dissolved in methylene chloride and the solution was washed three times with water, dried (MgSO4) and evaporated leaving the desired product as a yellow resin. NMR δ (200 MHz, CDCl3), 3.10 (dd, J=4.2 and 1.8, H3), 5.12 (d, J=1.8, H4).

EXAMPLE 7

P-nitrobenzyl-trans-2-(3-(1-t-butyldimethylsilyloxyethyl)-4-phenoxythiocarbonylthio-2-azetidinon-1-yl)acetate

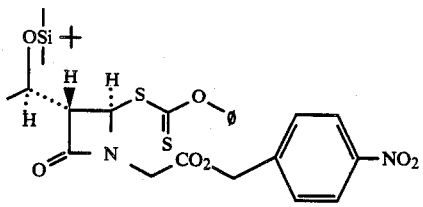

P-nitrobenzyl trans 2-[3-(1-t-butyldimethylsilyloxyethyl)-4-silverthio-2-azetidinon-1-yl)acetate (177 mg, 0.32 mmol) was dissolved in 2 ml of methylene chloride and the solution was cooled to 0°. Plenoxythiocarbonylchloride (43 μl, 0.32 mmol) and pyridine (26 μl) were added and the mixture was stirred for 20 minutes. The mixture was centrifuged and the supernatant liquid was concentrated and chromatographed on silica gel plates developed with toluene-ethyl acetate (9:1). The band at Rf 0.4 was isolated giving the desired product as a strawcolored oil. Yield, 85 mg, (46%). NMR δ (200 MHz, CDCl3), 3.34 (dd, J=6 and 2.8, H3), 5.84 (d, J=2.8, H4).

EXAMPLE 8

P-nitrobenzyl-trans-6-(1-t-butyldimethylsilyloxyethyl)-2-thioxo-penam-3-carboxylate

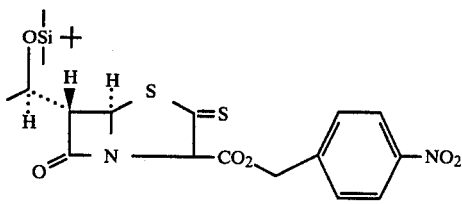

P-nitrobenzyl trans 2-(3-(1-t-butyldimethylsilyloxyethyl)-4-phenoxythiocarbonylthio-2-azetidinon-1-yl)acetate (74 mg, 0.125 mmol) was dissolved in 1 ml of dry tetrahydrofuran and the solution was cooled to −78°. Lithium hexamethyldisilazide (0.6 ml of 0.5M solution) was added and the solution was stirred for 20 minutes. The solution was diluted with methylene chloride (5 ml) then neutralized with glacial acetic acid (29 μl). The solution was extracted with pH 7 phosphate buffer and with water, then dried over MgSO4 and evaporated. The residue was purified by thin layer chromatography (2% methanol in chloroform) giving 33 mg (53%) of the desired product. NMR δ (200 MHz, CDCl3), 3.68 (dd, J=4 and 1, H6), 5.42 (s, H3), 5.89 (d, J=1, H5).

EXAMPLE 9

P-nitrobenzyl-trans-6-(1-t-butyldimethylsilyloxyethyl)-2-methylthio-penem-3-carboxylate

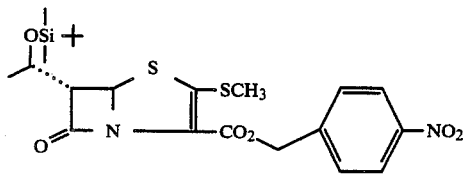

Lithium hexlamethyldisilazide (0.37 ml of a 0.174M solution) was added to a solution of P-nitrobenzyl trans-2-[3-(1-t-butyldimethylsilyloxyethyl)-4-phenoxythiocarbonylthio-2-azetidinon-1-yl)acetate (19 mg, 0.032 mmol) in 0.3 ml of dry tetrahydrofuran at −78°. After 20 minutes methyl iodide (20 μl) was added and the solution was allowed to warm to 0°. The reaction was continued at 0° for 30 minutes. The mixture was diluted with methylene chloride and washed with pH 7 phosphate buffer and with water and dried over magnesium sulfate. The solvent was evaporated and the residue purified by thin layer chromatography (eluent 9:1 toluene-ethyl acetate) to afford 10 mg of the desired compound. NMR (200 MMz, CDCl3), 2.54 (s, SCH3), 3.72 (dd, J=4.5 and 1.5, H6), 5.76 (d, J=1.5, H5).

EXAMPLE 10

Chiral Synthesis (+)-(3S,4R)-3-(1-R-t-butyldimethylsilyloxy)-4-triphenylmethylthio-2-azetidinone

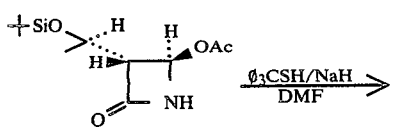

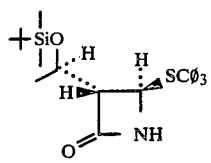

To a stirred suspension of 1.3 g (0.033 moles) of 61% NaH dispersion in 25 ml of sieve dried DMF at 0° C. under an atmosphere of nitrogen was added dropwise a solution of 9.12 g (0.033 moles) of trityl mercaptan in 50 ml of sieve dried DMF over a period of 23 minutes. The resulting mixture was stirred further at 0° C. under nitrogen for 10 minutes, after which time a solution of (3S,4R)-4-acetoxy-3-(1-R-t-butyldimethylsilyloxy)azetidinone 1 (8.62 g, 0.03 moles) in 50 ml of sieve dried DMF was added over a period of 20 minutes. The mixture was stirred further at 0° C. under nitrogen for 0.5 hours and was then poured onto a mixture of ice-H$_2$O and saturated, aqueous NH$_4$Cl solution and extracted wth Et$_2$O. The Et$_2$O extract was washed twice with H$_2$O and then with saturated NaCl solution, dried over anhydrous Na$_2$SO$_4$, filtered, and evaporated. Purification by column chromatography on 500 g EM-60 silica gel eluting with CH$_2$Cl$_2$ gives 12.9 g, (85%) of product; $[\alpha]_D$+3.7 (c 8, CHCl$_3$); mp. 94°–96.5° C.

EXAMPLE 11

Allyl-(3S,4R)-2-(1-R-t-butyldimethylsilyloxyethyl)-4-triphenylmethylthio-2-azetidinon-1-yl)acetate

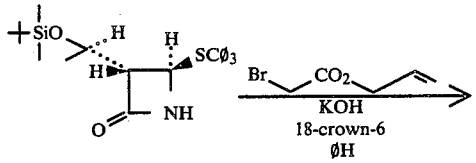

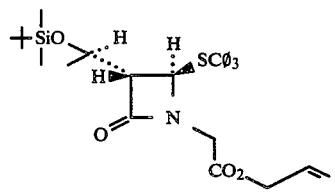

According to the procedure of T. Kamazaki, et al., Heterocycles, 15, 1101 (1981), 5.04 g (0.01 moles) of (+)-(3S,4R)-3-(1-R-t-butyldimethylsilyloxy)-4-triphenylmethylthio-2-azetidinone 2, 926 mg (0.0165 moles) of powdered KOH, and a catalytic amount of 18-crown-6 was stirred in 50 ml of benzene at ambient temperature and was treated with a solution of 2.67 g (0.015 moles) of allylbromoacetate in 30 ml benzene (added dropwise over 30 minutes) at ambient temperature for 5 hours. After this time the mixture was partitioned between EtOAc and ice-H$_2$O. The organic phase was separated, washed with saturated NaCl solution, dried over anhydrous Na$_2$SO$_4$, filtered and evaporated. Purification by column chromatography on 300 g of EM-60 silica gel eluting with CH$_2$Cl$_2$ and 2% EtOAc in CH$_2$Cl$_2$ gives 3.74 g (62%) of the product as a colorless oil; $[\alpha]_D$+0.8 (c 20, CHCl$_3$).

EXAMPLE 12

Allyl-(3S,4R)-2-(3-(1-R-t-butyldimethylsilyloxyethyl)-4-phenoxythiocarbonylthio-2-azetidinon-1-yl)acetate

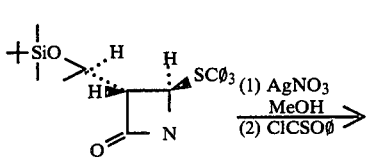

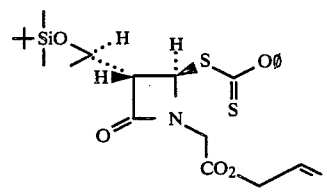

To a stirred solution of 3.74 g (6.2 mmoles) of allyl (3S,4R)-2-(3-(1-R-t-butyldimethylsilyloxyethyl)-4-triphenylmethlthio-2-azetidinon-1-yl)-acetate in 30 ml MeOH at 0° C. was added sequentially 738.4 mg (9.3 mmoles) of neat pyridine and then 45.6 ml of 0.15M AgNO$_3$ solution in MeOH. The resulting mixture was stirred at 0° C. under nitrogen for 0.5 hours after which time the mixture was concentrated in vacuo and partitoned between CH$_2$Cl$_2$ and ice-H$_2$O. The organic phase was separated, dried over anhydrous Na$_2$SO$_4$, filtered, evaporated, and dried in vacuo. The residue so obtained was dissolved in 30 ml CH$_2$Cl$_2$, stirred, cooled to 0° C., and treated sequentially with 500 μl of pyridine and 1.18 g (6.85 mmoles) of phenoxythio chloroformate. After stirring at 0° C. under an atmosphere of nitrogen for 20 minutes, the insolubles were removed by filtration through celite and washed well with EtOAc. The filtrate was partitioned between EtOAc, ice-H$_2$O, and 2N HCl. The organic phase was separated, washed with saturated NaCl solution, dried over anhydrous Na$_2$SO$_4$, filtered, and evaporated. Purification of the residue by chromatography on 100 g of EM-60 silica gel eluting with CH$_2$Cl$_2$-φMe (10:1) provides 2.23 g (72%) of the desired product, 4, as a yellow oil; $[\alpha]_D$+59.6 (c 13.6, CHCl$_3$).

EXAMPLE 13

Allyl-(5R,6S)-6-(1-R-t-butyldimethylsilyloxyethyl)-2-thioxopenam-3-carboxylate

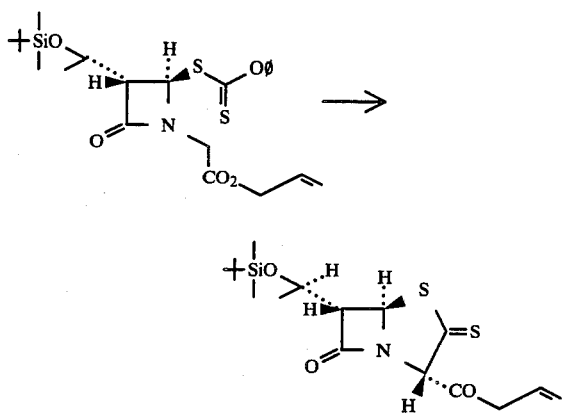

To a stirred solution of freshly prepared lithium hexamethyldisilazide (0.54 mmoles) in 5 ml anhydrous THF containing 100 μl of 1,3-dimethyl-2-imidazolidinone at −78° C. under a nitrogen atmosphere was added a solution of 96.6 mg (0.195 mmoles) of allyl (3S,4R)-2-(3-(1-R-t-butyldimethylsilyloxyethyl)-4-phenoxythiocarbonylthio-2-azetidinon-1-yl)acetate in 800 μl of anhydrous THF. The resulting mixture was stirred at −78° C. under nitrogen for 4 minutes and then was partitioned between EtOAc, ice-H2O aand 2N HCl. The organic phase was separated, washed with saturated NaCl solution, dried over anhydrous Na2SO4, filtered, and evaporated. The residue was purified by plate layer chromatogrphy [one development CH2Cl2] to give 53.2 mg (68%) of thioxopenam as an orange oil; [α]$_D$−31.70 (C 4.3, CHCl3); λ max EtOH=316 nm; λ max Et3N, EtOH=353.2 nm.

EXAMPLE 14

Allyl-(5R, 6S)-6-(1-R-hydroxyethyl)-2-thioxopenam-3-carboxylate

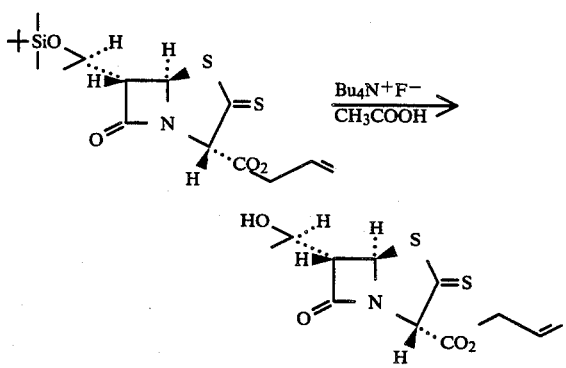

To a stirred solution of Allyl (5R, 6S)-6-(1-R-t-butyldimethylsilyloxyethyl)-2-thioxopenam-3-carboxylate (41.7 mg) 0.1 mmol) in 1 ml of tetrahydrofuran at 0° was added glacial acetic acid (70 μl) followed by tetrabutylammonium fluoride (1M in TMF, 0.3 ml). The solution was stirred at room temperature for 24 hours then diluted with 5 ml of methylene chloride and extracted three times with 0.1M PH7 phosphate buffer. The methylene chloride solution was dried (MgSO4) and evaporated and the residue purified by plate-layer chromatography (5% MeOH in CHCl3), providing 20 mg of the de-silyated thioxo penam allyl ester or a yellow oil. NMR (200 MHz, CDCl3), 3.65 (dd, J=1.5 and 6.5, H-6), 5.38 (S, H-3), 5.92 (d, J=1.5, H-5) [α]$_D$+22° (C 1.6, MeOH).

EXAMPLE 15

P-nitrobenzyl-5R, 6S)-6-(1-R-hydroxyethyl)-2-thioxopenam-3-carboxylate

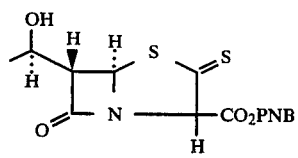

Following the procedure in Example 14 substituting p-nitrobenzyl (5R, 6S)-6-(1-R-t-butyldimethyl silyloxyethyl)-2-thioxopenam-3-carboxylate for the corresponding allyl ester, there is obtained the de-silyated thioxopenam p-nitrobenzyl ester.

EXAMPLE 16

Allyl-(5R,6S)-6-(1-R-t-butyldimethylsilyloxyethyl)-2-cyanomethylthio-penem-3-carboxylate

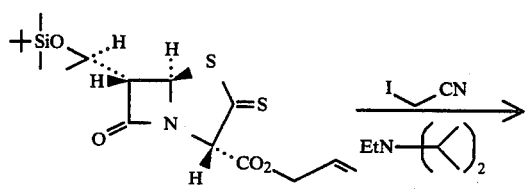

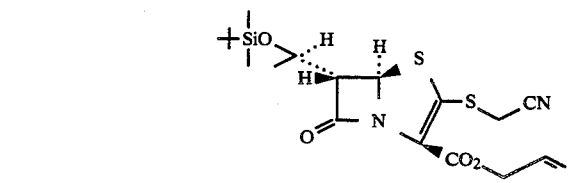

To a stirred solution of 75.5 mg (0.188 mmoles) of allyl (5R,6S)-6-(1-R-t-butyldimethylsilyloxyethyl)-2-thioxopenam-3-carboxylate in 2 ml CH2Cl2 at 0° C. was added sequentially 24.3 mg (0.188 mmoles) of diisopropylethylamine and 31.4 mg (0.188 mmoles) of iodoacetonitrile. The mixture was stirred under an atmosphere of nitrogen at 0° C. for 10 minutes and was then partitioned between EtOAc, ice-H2O, and B 2N HCl. The organic phase was separated, washed with saturated NaCl solution, dried over anhydrous Na2SO4, filtered and evaporated. The residue was purified by plate layer chromatography [one development CH2Cl2] to give 62.0 mg (75%) of the cyanomethyl penem. Recrystallization from Et2O-hexanes gives mp. 91°-92° C.; [α]$_D$+97.5 (C 2.49, CHCl3).

EXAMPLE 17

General procedure for the alkylations of 2-Thioxopenams. Preparation of Allyl-(5R, 6S)-6-[1-(R)-t-butyldimethylsilyloxyethyl]-2-cyanonethylthiopen-2-em 3-carboxylate To a stirred solution of allyl (5R, 6S)-6-[1-R-t-butyldimethylsilyloxyethyl)-2-thioxopenam-3-carboxylate (75.5 mg, 0.19 mmol) in 2 ml of methylene chloride at 0° C. was added sequentially 24.3 mg (0.19 mmol) of diisopropylethylamine and 31.4 mg (0.19 mmol of iodoacetonitrile. The mixture was stirred at 0° C. for 10 minutes and then partitioned between ethylacetate, ice-$H_2O$ and 2N HCl. The organic phase was dried, and evaporated and the residue purified by plate layer chromotography affording 62 mg (75%) of the titled penem. IR($CH_2Cl_2$) 1799, 1712, 1684 cm$^{-1}$; NMR 0.09 (S, 6H), 0.9(S, 9H), 1.28 (d, J=6.5 Hz, 3H), 3.69 (d, J=18 HZ, 1H), 3.76 (d, J=18 HZ, 1H), 3.84 (dd, J=1.5, 4.5 HZ 1H), 4.3 (m, 1H), 4.76 (m, 2H), 5.3 (m, 1H), 5.46 (m, 1H) 5.8 (d, J=1.5 HZ) and 5.96 (m, 1H); λ max 338 nm, 252.5 nm; MS m/e 440(M+), 383, 143, 73; [α]$_D$+97.5 (C 2.49); m.p. 91°-92° C. ($Et_2O$-hexane).

TABLE I
Alkylations of 2-Thioxopenams to Penems

| Alkyl Halide[a] | R | T(h) | Solvent, T° C. | Yield |
|---|---|---|---|---|
| ClCH$_2$COCH$_3$ | CH$_2$COCH$_3$ | 1 | CH$_2$Cl$_2$, 0° | 80 |
| BrCH$_2$CH$_3$ | CH$_2$CH$_3$ | 19 | CH$_2$Cl$_2$, 0° | 76 |
| BrCH$_2$CH$_2$CH$_3$ | CH$_2$CH$_2$CH$_3$ | 1.5 | DME, 60° | 80 |
| CH$_3$CHBrCH$_2$CH$_3$ | CH$_3$<br>|<br>—CHCH$_2$CH$_3^b$ | 0.5 | DMF, 80° | 77 |
| (CH$_3$)$_3$CBr[c] | C(CH$_3$)$_3$ | 5 | DME, 60° | 30 |
| ClCH$_2$CH$_2$CH$_2$CH$_3$ | CH$_2$CH$_2$CH$_2$CH$_3$ | 21 | DME, 60° | 10 |
| ICH$_2$CN | CH$_2$CN | 0.2 | CH$_2$Cl$_2$, 0° | 75 |

[a]Isolate Yield
[b]1:1 Mixture of diasteromers
[c]1 equiv. AgOSO$_2$CF$_3$ added

What is claimed is:
1. A process for preparing:

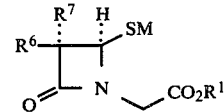

consisting essentially of the steps of treating:

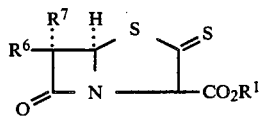

with a thiophilic metal reagent selected from the group consisting of salts of silver, mercury and thallium to produce:

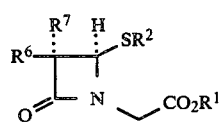

followed by treating with a halothiocarbonate ester of the formula:

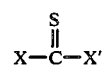

wherein:
X' is chloro, bromo, and X is phenoxy, phenylthio, alkylthio, having 2–7 carbon atoms
to yield:

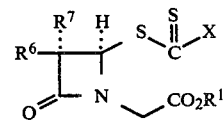

followed by cyclizing in the presence of base; wherein:
R$^6$ and R$^7$ are independently selected from: hydrogen; R$^9$NH—(R$^9$ is acyl or H); substituted and unsubstituted: alkyl, alkenyl, alkynyl, having 1–6 carbon atoms; phenyl; heterocyclyl, heteroaryl, having 1–4 heteroatoms selected from O,N,S; cycloalkyl, and cycloalkenyl; wherein said substituent or substituents are selected from: halo (chloro, bromo, fluoro, iodo), hydroxyl, cyano, carboxyl, amino, and the above-recited values for R$^6$/R$^7$;
R$^2$, is a group which potentially forms a stable carbonium ion; M is a thiophilic metal selected from the group consisting of silver, mercury and thallium; and R$^1$ is a removable protecting group, or a pharmaceutically acceptable ester moiety;
X is a leaving group.
2. The process according to claim 1;
wherein:
R$^6$ and R$^7$, are selected from:

| | |
|---|---|
| —H | OR<br>|<br>—CHCH$_2$F |
| —CH$_3$ | OR<br>|<br>—CHCH$_3$ |
| —CH$_2$CH$_3$ | OR<br>|<br>—C—CF$_3$<br>|<br>H |
| —CH$_2$CH$_2$OR | |
| —CH$_2$OR | |
| —CH(CH$_3$)$_2$ | OR<br>| |
| —OCH$_3$ | —CHCH$_2$Cl |
| —CH$_2$CH$_2$Cl | OR<br>| |
| —C(OR)(CH$_3$)$_2$ | —C—CH$_3$<br>|<br>CH$_3$ |
| —CHCH$_3$<br>|<br>F | OR<br>|<br>—C—◁ |

-continued

| OR |
|---|
| \| |
| —CHCH$_2$CH$_3$ |

R=H, protecting group.

3. The process according to claim 1; wherein $R^6$ is H and $R^7$ is alkyl having 1–6 carbon atoms, or hydroxy- and protected hydroxyl-substituted alkyl.

4. The process according to claim 1 wherein $R^6$ is H; and $R^7$ CH$_3$CH(OR)—wherein R is H or a removable protecting group.

5. The process according to claim 1 wherein M is silver and $R^2$ is trityl.

6. A process for preparing:

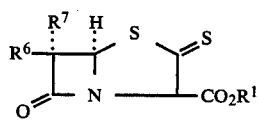

comprising cyclizing:

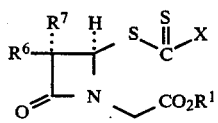

in the presence of base; wherein $R^6$ and $R^7$ are independently selected from: hydrogen; $R^9$NH—($R^9$ is acyl or H); substituted and unsubstituted: alkyl, alkenyl, alkynyl, having 1–6 carbon atoms; aryl, such as phenyl; heterocyclyl, heteroaryl, having 1–4 heteroatoms selected from O,N,S; cycloalkyl, and cycloalkenyl; wherein said substituent or substituents are selected from: halo (chloro, bromo, fluoro, iodo), hydroxyl, cyano, carboxyl, amino, and the above-recited values for $R^6/R^7$; and $R^1$ is a removable protecting group, or a pharmaceutically acceptable ester moiety; X is a leaving group.

7. A process for preparing:

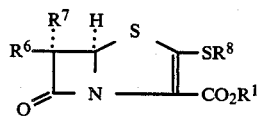

comprising treating:

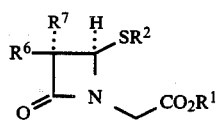

with a thiophilic metal reagent to produce:

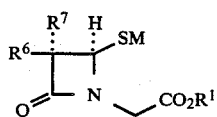

followed by treating with a halothiocarbonate ester to yield:

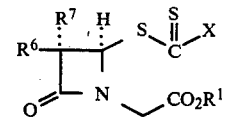

followed by cyclizing in the presence of base; reaction with $R^8X^\circ$; and deblocking wherein:

$R^6$ and $R^7$ are independently selected from: hydrogen; $R^9$NH—($R^9$ is acyl or H); substituted and unsubstituted: alkyl, alkenyl, alkynyl, having 1–6 carbon atoms; phenyl; heterocyclyl, heteroaryl, having 1–4 heteroatoms selected from O,N,S; cycloalkyl, and cycloalkenyl; wherein said substituent or substituents are selected from: halo (chloro, bromo, fluoro, iodo), hydroxyl, cyano, carboxyl, amino, and the above-recited values for $R^6/R^7$;

$R^2$, in functional terms, is a group which potentially forms a stable carbonium ion;

M is a thiophilic metal; and $R^1$ is a removable protecting group, or a pharmaceutically acceptable ester moiety;

X is a leaving group; $R^8X^\circ$ is an alkylating agent taken to establish $R^8$, which is substituted and unsubstituted: alkyl, aryl, aralkyl, cycloalkyl radical known in the antibiotic penem art.

8. A process for preparing:

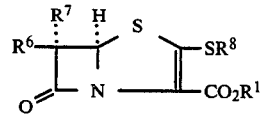

comprising cyclizing:

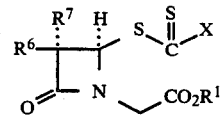

in the presence of base; to form

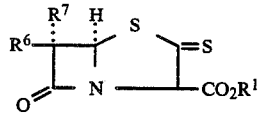

followed by treatment with an alkylating agent $R^8X^\circ$; wherein $R^6$ and $R^7$ are independently selected from: hydrogen; $R^9$NH—($R^9$ is acyl or H); substituted and unsubstituted: alkyl, alkenyl, alkynyl, having 1–6 carbon atoms; aryl, such as phenyl; heterocyclyl, heteroaryl, having 1–4 heteroatoms selected from O,N,S; cycloalkyl, and cycloalkenyl; wherein said substituent or substituents are selected from: halo (chloro, bromo, fluoro, iodo), hydroxyl, cyano, carboxyl, amino, and the above-recited values for $R^6/R^7$; and $R^1$ is a removable protecting group, or a pharmaceutically acceptable ester moiety; and X is a leaving group.

* * * * *